US00PP12107P2

(12) United States Plant Patent
Skotak

(10) Patent No.: US PP12,107 P2
(45) Date of Patent: Oct. 2, 2001

(54) NEOREGELIA PLANT NAMED 'ZOË'

(75) Inventor: Chester Skotak, Alajuela (CR)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/285,075

(22) Filed: Apr. 2, 1999

(51) Int. Cl.[7] ..... A01H 5/00
(52) U.S. Cl. ..... Plt./370
(58) Field of Search ..... Plt./370

*Primary Examiner*—Bruce R. Campell
*Assistant Examiner*—Kent L. Bell
(74) *Attorney, Agent, or Firm*—Foley & Lardner

(57) ABSTRACT

A distinct Neoregelia plant named 'Zoë' characterized by its small size measuring 15 cm in height and approximately 22 cm in diameter when grown in 12.5-cm pots. The leaves have a wine color with the leaf margins in the greyed-purple group (RHS 187 A); leaves of the rosette retain their color through the life cycle of the plant; 'Zoë' produces large numbers of stoloniferous offsets and the stolons are approximately 15 cm long.

2 Drawing Sheets

BACKGROUND OF THE INVENTION

The present invention comprises a new and distinct cultivar of Neoregelia hybrid, botanically known as Neoregelia and hereinafter referred to by the cultivar name 'Zoë'. Neoregelia species are tank epiphytes with stemless inflorescences and flowers that barely rise above the water in the center of the plants. 'Zoë' can be advantageously grown as a single-pot or hanging-basket plant in order to display its symmetrically rosette plant form.

'Zoë' is characterized by its small plant size and grayed-purple of its leaf margins (RHS 187 A). The leaf margin at the sheath is RHS 137 C. The center variegation of the leaf is RHS 187 D. 'Zoë' is a stoloniferous plant that produces leaves with an overall wine color appearance.

'Zoë' is a product of a planned breeding program and was originated from a cross made in Balsa, Costa Rica, in 1989. The female parent (unpatented) was an unnamed plant of (*Neoregelia carolinae lineata*×Neoregelia 'Fireball')×Neoregelia 'Fireball'. The male parent (unpatented) was Neoregelia 'Fireball', an unnamed species from Brazil that is known as *Neoregelia schultesiana* in Europe. 'Zoë' was discovered and selected as a flowering plant within the progeny of the stated cross by the inventor, Chester Skotak, Jr., in 1991, in a controlled environment in a nursery in Balsa, Costa Rica. 'Zoë' was first asexually reproduced in Balsa, Costa Rica in 1991, by division. Subsequent asexual reproduction by vegetative propagation has demonstrated that the combination of characteristics as herein disclosed for the new cultivar are firmly fixed and reproduces true to type through successive generations of asexual reproduction.

BRIEF DESCRIPTION OF THE INVENTION

The following traits have been repeatedly observed and are determined to be basic characteristics of 'Zoë' which in combination distinguish this Neoregelia as a new and distinct cultivar:

1. Small size measuring approximately 15 cm in height when grown in a 12.5-cm pot and approximately 22 cm in diameter when fully grown;

2. A brilliant wine color with the leaf margins in the greyed-purple group (RHS 187 A);

3. Leaves of the rosette which retain their color through the life cycle of the plant with the center color having a layer of gray-purple 185 B when in flower; and 4. Large numbers of stoloniferous offsets with stolons approximately 15 cm long.

'Zoë' has not been observed under all possible environmental conditions. The phenotype of the new cultivar may vary significantly with variations in environment such as temperature, light intensity, and daylength, without any variation in the genotype of the plant.

The new variety Neoregelia 'Zoë' can be compared to Neoregelia 'Fireball', an unnamed species from Brazil known as *Neoregelia schultesiana* in Europe. 'Zoë' has a well-developed rossette of leaves and is larger than Neoregelia 'Fireball'. 'Zoeë' is also variegated and has finely serrated margins whereas Neoregelia 'Fireball' is not variegated and is almost spineless. The female parent cultivar is a larger plant in overall appearance, and the wine coloration in the leaves is not as strong.

BRIEF DESCRIPTION OF THE DRAWING

The accompanying photographs illustrate a 'Zoë' plant following growth under appropriate growing conditions, with colors being as true as possible with illustrations of this type.

Sheet 1 is a side view of the plant grown in Balsa, Costa Rica.

Sheet 2 is a top view of the plant grown in Evergem, Belgium.

DETAILED BOTANICAL DESCRIPTION

The following observations, measurements and values describe plants grown in Balsa, Costa Rica, Evergem, Belgium and Apopka, Fla., USA, under greenhouse conditions which closely approximate those generally used in horticultural practice. The age of the plants described is 12 months from asexual reproduction. Color references are made to The Royal Horticultural Society (R.H.S.) Colour Chart, except where general colour terms of ordinary significance are used.

Classification:

*Botanical.*—*Neoregelia hybrid*, cv. 'Zoë'.

*Commercial.*—Neoregelia 'Zoë'.

Parentage:

*Male parent.*—Neoregelia 'Fireball'.

*Female parent.*—An unnamed plant of (*Neoregelia carolinae lineata*×Neoregelia 'Fireball')×Neoregelia 'Fireball'.

Propagation: Vegetative by removal of offsets (asexual).

Plant description:

*Size.*—Approximately 15 cm tall when grown in 12.5-cm pots, and approximately 22 cm in diameter when fully grown.

*Growth habit.*—Spreading rosette, very stoloniferous.

*Vigor.*—It takes 9 to 12 months, for one plant with 2 to 3 shoots, to produce a finished plant from initial planting, in Belgium and Holland.

Leaves:

*Apex.*—Blades lingulate, recurved, broadly rounded and apiculate.

*Size.*—Length is approximately 14 cm to 16 cm; width is approximately 3 cm in the middle and 1.5 cm at the tip.

*Margin.*—Finely serrated.

*Surface* (*upper and lower*) *texture.*—Smooth.

*Veins or ribs.*—None.

*Color.*—Leaves are variegated longitudinally with light green (RHS 150C) and dark green (RHS 137B) colors with a margin of (RHS 137C) at the sheath. When grown under shade house conditions in Balsa, Costa Rica the leaf margins are in the greyed-purple group (RHS 187A) and when grown in a greenhouse in Belgium, the leaf margins are in the yellow-green group (RHS 146A). The basal portion of the leaves are variegated with the same light and dark green colors overlaid with a red-purple coloration of (RHS 187D) (Color designations represent both upper and lower surfaces).

*Number.*—Approximately 25 per plant.

Rosette:

*Leaves forming the socket.*—Approximately 1.5 cm in overall diameter.

*Color.*—The leaves have little or no color when in bloom.

*Flowers.*—Arrangement: Inflorescence is central, sunk in the center of the rosette, simple and with many flowers. Color: Petal color is violet-blue (RHS 90 A) towards the apex with a white base (upper surface), and is violet-blue (RHS 90D) (lower surface). Petals: Lanceolate, acuminate about equaling the sepals. Sepals: Asymmetric, acuminate to 10 mm in length, 3 mm wide at base, color is yellow-green RHS 149 C (Both surfaces). Scape: Typically 65 mm in overall length, diameter 12 mm, color is yellow-green RHS 149 C (upper portion) and white RHS 155 D (lower portion). Blooming response: Initiated by ethylene treatment, approximately. Lasting quality of individual bloom: Approximately one day.

*Flowering season.*—Sporadic flowering all year round, no known flowering season.

Reproductive organs:

*Stamens.*—White.

*Pistils.*—White. Ovary is ellipsoid, approximately 10 mm long and 3 mm in diameter.

*Anthers.*—RHS White 155A; 6 Anthers measuring 5 mm in length attached to the base of the petals by 2 filaments; 2 Anthers for each of the 3 petals.

*Style.*—Approximately 8 mm long, RHS White 155C.

*Stigma.*—Formed in a corkscrew with a measurement of 2 mm long.

*Pollen.*—Grainy and plentiful, RHS White 155 A.

*Pistils.*—1 per flower.

Disease resistance: Good resistance to fungi and insects exhibited in Costa Rica.

General observations: 'Zoë' produces large numbers of offsets. Individual plants may produce up to 10 offsets per mature plant.

Winter hardiness: 'Zoë is not winter hardy and will show cold damage at 32 degrees Fahrenheit.

I claim:

1. A new and distinct Neoregelia plant named 'Zoë', substantially as illustrated and described herein.

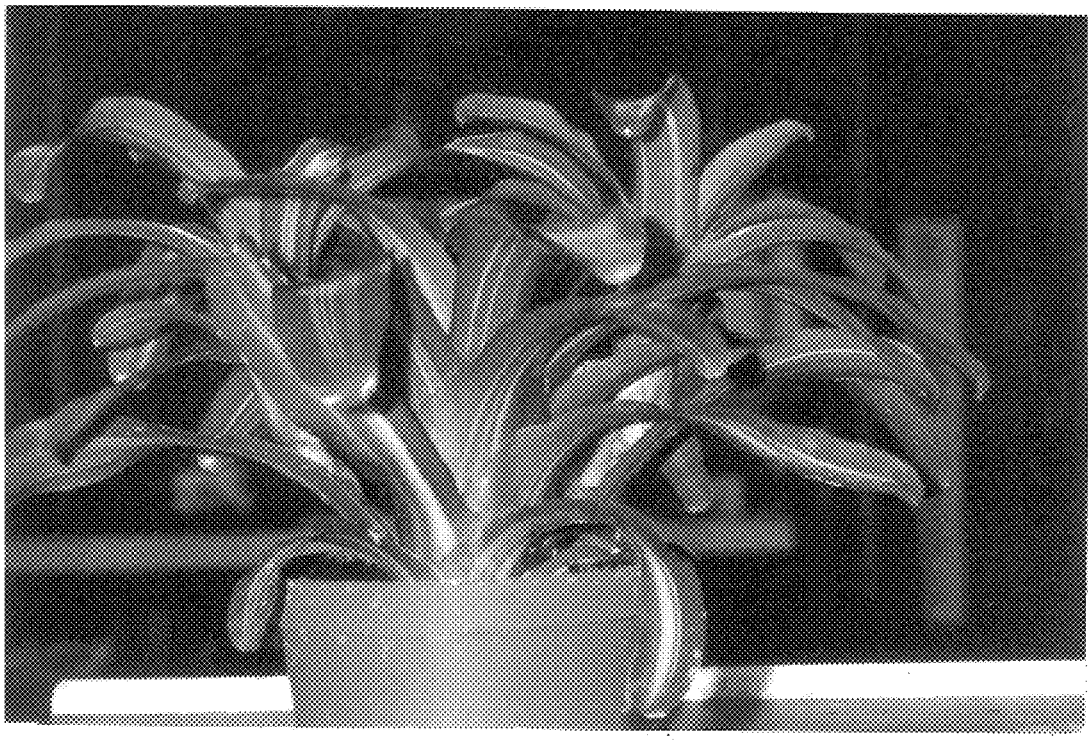

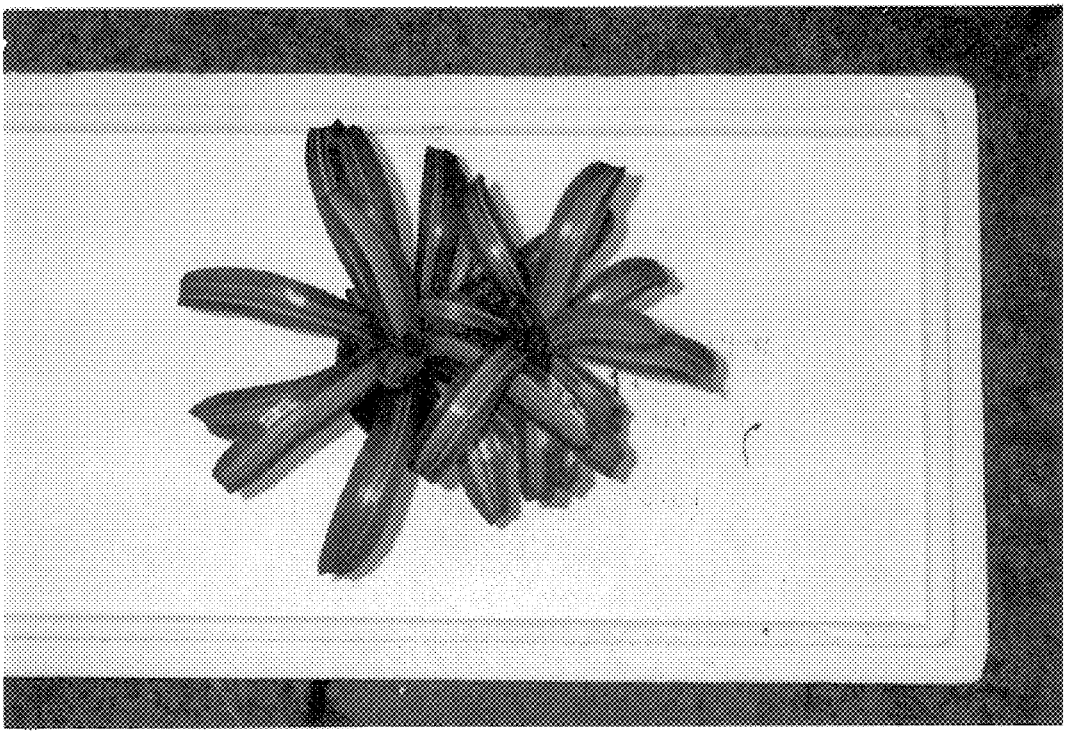

* * * * *